United States Patent
Yagihara et al.

(10) Patent No.: US 6,541,642 B1
(45) Date of Patent: Apr. 1, 2003

(54) PROCESS FOR THE PREPARATION OF (E)-3-(1-PROPENYL)ISOXAZOLINE

(75) Inventors: Tomio Yagihara, Kanagawa (JP); Michinori Takebayashi, Kanagawa (JP); Hiroyuki Yamanaka, Kanagawa (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 09/937,438

(22) PCT Filed: Mar. 28, 2000

(86) PCT No.: PCT/JO00/01901
§ 371 (c)(1),
(2), (4) Date: Sep. 26, 2001

(87) PCT Pub. No.: WO00/58290
PCT Pub. Date: Oct. 5, 2000

(30) Foreign Application Priority Data

Mar. 29, 1999 (JP) .......................................... 11-085076

(51) Int. Cl.[7] ............................................. C07D 261/04
(52) U.S. Cl. ...................................................... 548/240
(58) Field of Search ......................................... 548/240

(56) References Cited

U.S. PATENT DOCUMENTS

| 4,889,551 A | 12/1989 | Oda et el. ....................... 71/88 |
| 6,124,469 A | 9/2000 | Rheinheimer et al. ...... 548/240 |
| 6,165,944 A | 12/2000 | von Deyn et al. .......... 504/271 |

FOREIGN PATENT DOCUMENTS

WO  PCT/JP00/01901  10/2000

OTHER PUBLICATIONS

Andrisano, R; Pappalardo, G; "Azione dell'idrossilamina sulle basi di Mannich da furfuriliden–acetaone" GAZZ. CHM. ITAL., vol. 88, 1958, pp. 174–183.
Supplementary European Search Report, Application No. Ep 00 91 1415, 2002.
J. Org. Chem., 62, pp. 3671–3677 (1997).
Chemistry Letters, The Chemical Society of Japan, pp. 183–186 (1986).

*Primary Examiner*—Brenda Coleman
(74) *Attorney, Agent, or Firm*—Dennis G. LaPointe

(57) ABSTRACT

A process for the preparation of (E)-3-(1-propenyl)-2-isoxazoline, characterized by reacting crotonaldehyde with hydroxylamine to form an oxime, and then converting the oxime into a nitrile oxide while reacting the nitrile oxide with ethylene.

1 Claim, No Drawings

PROCESS FOR THE PREPARATION OF (E)-3-(1-PROPENYL)ISOXAZOLINE

This application is a national stage entry under 35 U.S.C. § 371 of PCT/JR00/01901 filed Mar. 28, 2000.

TECHNICAL FIELDS

The present invention relates to a process for the preparation of (E)-3-(1-propenyl)-2-isoxazoline useful as an intermediate for producing agricultural chemicals, drugs and others.

BACKGROUND ART

Only one known process for the preparation of (E)-3-(1-propenyl)-2-isoxazoline is that described by P. A. Wade, et al in J. Org. Chem., 62, 3671–3677(1997): The E isomer is obtained by reduction of 3-(1-propenyl)-2-isoxazoline (A), followed by isomerization of the produced mixture of Z and E isomers. The compound (A) is produced from nitroisoxazoline and propyne lithium with many steps, being very expensive.

DISCLOSURE OF THE INVENTION

It is an object of the present invention to provide an industrially advantageous process for the preparation of (E)-3-(1-propenyl)-2-isoxazoline.

The present invention relates to a process for the preparation of (E)-3-(1-propenyl)-2-isoxazoline, characterized by a reaction of crotonaldehyde with hydroxylamine, followed by a reaction of the produced oxime, while changing to nitrile oxide, with ethylene.

FORMS TO IMPLEMENT THE INVENTION

A process of the present invention is described below:

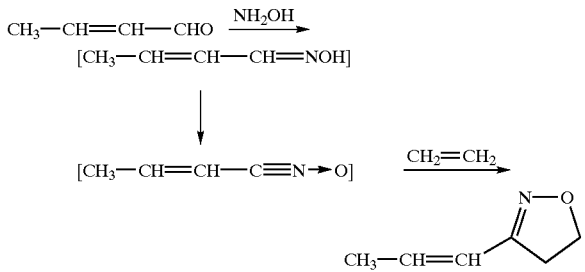

The present invention relates to a method of obtaining (E)-3-(1-propenyl)-2-isoxazoline in a way that crotonaldehyde is treated with hydroxylamine in a solvent and then ethylene is blown into the produced oxime while changing to nitrile oxide. It is possible to isolate the oxime. It is however preferable to use the solution itself in the next reaction without isolating it.

An aqueous solution of hydroxylamine or its hydrochloride can be used.

Any solvent can be used for the reaction if it does not react with nitrile oxide. Examples of solvents used include chlorine compounds such as chloroform, aliphatic hydrocarbons such as hexane, and aromatic hydrocarbons such as benzene and toluene.

An oximation reaction can be carried out at a temperature of 40° C. or below. However, it is generally preferable to do at 10° C. or below.

Examples of agents used to generate nitrile oxide include oxidizing agents such as sodium hypochlorite, and halogenating agents such as N-chlorosuccinimide (NCS). When the latter is used, a weak base, such as potassium hydrogen carbonate, is required.

A reaction of nitrile oxide with ethylene is usually carried out in a way that ethylene is blown into a solution containing nitrile oxide at the atmospheric pressure.

In the present invention, ordinary work-up are applied after the completion of the reactions. It is possible to separate and purify the product by distillation or column chromatography (with a mixed solvent of ethyl acetate and n-hexane).

IR, NMR, MS and other means were used to identify the products.

BEST FORMS TO IMPLEMENT THE INVENTION

The present invention is described in more detail in reference to an example.

EXAMPLE

Preparation of (E)-3-(1-propenyl)-2-isoxazoline

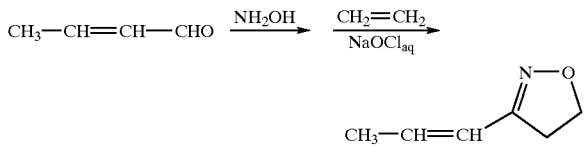

70 ml of chloroform was added to 7.0g of crotonaldehyde, and 7.3g of a 50% aqueous solution of hydroxylamine was dropped at 0° C. over 20 minutes while cooling with ice. Further, the solution was stirred at the same temperature for 30 minutes, and at room temperature for an hour. The reaction solution was separated. Ethylene was blown into the chloroform layer at 0° C. for 10 minutes while cooling with ice. Then, while blowing ethylene in, 44.7 g of a 10% aqueous solution of sodium hypochlorite was dropped over 30 minutes at 0C. Further, ethylene was blown in at the same temperature for 30 minutes, and the solution was stirred at 0° C. to room temperature for 2 hours. After the completion of the reaction, 50 ml of water was added and the solution was separated. The chloroform layer was dried over anhydrous magnesium sulfate, filtrated, concentrated under reduced pressure, and purified with column chromatography (with ethyl acetate:n-hexane=3:7) to give 5.29 g (yield: 47.7%) of the title compound. The product was distilled, having a boiling point of 40° C. (0.1 mmHg). This value was the same as that described in J. Org. Chem., 62, 3671–3677 (1997).

INDUSTRIAL APPLICABILITY

According to the present invention, (E)-3-(1-propenyl)-2-isoxazoline can be prepared using inexpensive crotonaldehyde as a starting material by a simple method.

(E)-3-(1-propenyl)-2-isoxazoline can be used as a starting material for producing 3-(isoxazolin-3-yl)-benzoic acids, which are intermediates to produce herbicides disclosed in WO 96/26206 and WO 98/31681.

An isoxazoline ring produces an amino alcohol by reduction and hydroxyketone by hydrolysis. Therefore, (E)-3-(1-propenyl)-2-isoxazoline is an extremely important compound as a precursor, and furthermore can be used as a dienophile for a Diels-Alder reaction. Compounds derived from (E)-3-(1-propenyl)-2-isoxazoline become intermediates for physiologically active substances.

What is claimed:

1. A process for the preparation of (E)-3-(1-propenyl)-2-isoxazoline by a reaction of crotonaldehyde with hydroxylamine, followed by a reaction of the produced oxime, while changing to nitrile oxide, with ethylene.

* * * * *